United States Patent
Lovmar

(10) Patent No.: US 12,420,058 B2
(45) Date of Patent: Sep. 23, 2025

(54) REUSABLE HYDROPHILIC URINARY CATHETER ASSEMBLY

(71) Applicant: DENTSPLY IH AB, Mölndal (SE)

(72) Inventor: Martin Lovmar, Mölndal (SE)

(73) Assignee: Dentsply Sirona Inc., York, PA (US)

( * ) Notice: Subject to any disclaimer, the term of this patent is extended or adjusted under 35 U.S.C. 154(b) by 6 days.

(21) Appl. No.: 17/702,214

(22) Filed: Mar. 23, 2022

(65) Prior Publication Data

US 2022/0305233 A1     Sep. 29, 2022

(30) Foreign Application Priority Data

Mar. 23, 2021   (EP) ..................................... 21164294

(51) Int. Cl.
  *A61M 25/00* (2006.01)
  *A61L 2/18* (2006.01)

(52) U.S. Cl.
  CPC ........... *A61M 25/0043* (2013.01); *A61L 2/18* (2013.01); *A61M 25/0017* (2013.01); *A61M 2025/0019* (2013.01); *A61M 2025/0056* (2013.01)

(58) Field of Classification Search
  CPC .......... A61M 25/0043; A61M 25/0017; A61M 2025/0056
  See application file for complete search history.

(56) References Cited

U.S. PATENT DOCUMENTS

| | | | |
|---|---|---|---|
| 4,754,877 A | 7/1988 | Johansson et al. | |
| 2007/0292595 A1* | 12/2007 | Nielsen | A61L 29/085 427/2.3 |
| 2008/0203592 A1* | 8/2008 | Qiu | G02B 1/043 264/2.6 |
| 2014/0190846 A1* | 7/2014 | Belt | A61L 29/085 53/431 |
| 2015/0065998 A1* | 3/2015 | Nielsen | A61M 25/0045 604/523 |

(Continued)

FOREIGN PATENT DOCUMENTS

| | | |
|---|---|---|
| CN | 117042819 A | 11/2023 |
| EP | 0093093 A1 | 11/1983 |

(Continued)

OTHER PUBLICATIONS

Extended European Search Report mailed Sep. 10, 2021 for European Patent Application No. 21164294.7.

(Continued)

*Primary Examiner* — Rebecca E Eisenberg
*Assistant Examiner* — Nhu Q. Tran
(74) *Attorney, Agent, or Firm* — SCHWEGMAN LUNDBERG & WOESSNER, P.A.

(57) ABSTRACT

A reusable urinary catheter assembly comprises a storage container defining a cavity, a hydration liquid and a reusable urinary catheter. The hydration liquid includes a disinfection medium and a hydrophilic polymer. The viscosity of the hydration liquid is 40 cP or lower. The reusable urinary catheter includes a shaft, and at least a part of the shaft is provided with a hydrophilic surface. During storage, the shaft is enclosed within the cavity in a storage position. The hydration fluid hydrates and regenerates the hydrophilic surface and disinfects the catheter. The catheter is configured to be repeatedly inserted into and removed from the storage container.

25 Claims, 1 Drawing Sheet

(56) References Cited

U.S. PATENT DOCUMENTS

| | | | |
|---|---|---|---|
| 2015/0246352 A1* | 9/2015 | Bullington | A61B 50/33 422/546 |
| 2019/0167849 A1* | 6/2019 | McBurney | A61L 29/143 |
| 2020/0001049 A1* | 1/2020 | House | A61M 25/0113 |
| 2021/0275727 A1* | 9/2021 | Farrell | A61M 25/0009 |
| 2022/0226603 A1* | 7/2022 | Murray | A61L 2/18 |
| 2022/0226605 A1* | 7/2022 | Murray | A61M 25/0045 |

FOREIGN PATENT DOCUMENTS

| | | |
|---|---|---|
| EP | 0217771 A1 | 4/1987 |
| JP | 2009-242348 A | 10/2009 |
| JP | 2024511457 A | 3/2024 |
| KR | 20230160241 A | 11/2023 |
| WO | 2011/112478 A1 | 9/2011 |
| WO | 2013/017547 A1 | 2/2013 |
| WO | 2015/074730 A1 | 5/2015 |
| WO | 2020/006527 A1 | 1/2020 |
| WO | 2020163859 A2 | 8/2020 |
| WO | 2020/252003 A1 | 12/2020 |
| WO | 2020/252032 A1 | 12/2020 |
| WO | 2020/252045 A1 | 12/2020 |
| WO | 2020/263859 A1 | 12/2020 |
| WO | WO-2021076512 A1 * | 4/2021 ............. A61L 27/50 |

OTHER PUBLICATIONS

Database WPI, Week 200975, Thomson Scientific, London, GB; an 2009-Q20584, XP002804071.

Extended European Search Report from European Patent Application No. 24154718.1 dated Jun. 5, 2024.

"International Application Serial No. PCT/EP2022/057446, International Preliminary Report on Patentability mailed Oct. 5, 2023", 8 pgs.

"International Application Serial No. PCT/EP2022/057446, International Search Report mailed Jun. 23, 2022", 4 pgs.

"International Application Serial No. PCT/EP2022/057446, Written Opinion mailed Jun. 23, 2022", 6 pgs.

* cited by examiner

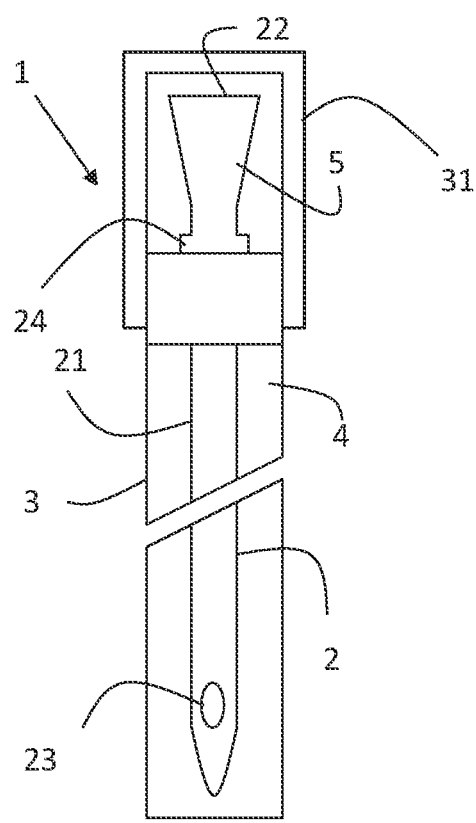

REUSABLE HYDROPHILIC URINARY CATHETER ASSEMBLY

CROSS-REFERENCE TO RELATED APPLICATIONS

This patent document claims the benefits and priority of European Patent Application No. 21164294.7, filed on Mar. 23, 2021, which is incorporated herein by reference in its entirety.

TECHNICAL FIELD OF THE INVENTION

The present invention relates to a reusable urinary catheter assembly. The invention also relates to a method for preparing a reusable hydrophilic urinary catheter for further use, and to a hydration liquid for regeneration, disinfection and activation of a reusable hydrophilic urinary catheter.

BACKGROUND

The disclosed embodiments relate to urinary catheter assemblies. Urinary catheters are commonly used for draining urine from the bladder. Urinary catheters can be of an indwelling type, for long term use, such as days or even weeks, or for intermittent use, whereby the catheters are used for a single draining procedure, typically lasting a few minutes. Intermittent urinary catheters are, e.g., used by a large group of persons for self-catheterization, which is a daily-life procedure, taking place several times a day. Typically, catheters for intermittent catheterization are used by patients suffering from urinary retention, due to e. g. spinal cord injury, multiple sclerosis or prostatic hyperplasia. Using an intermittent catheter, the bladder may be drained through a natural or artificial urinary canal. Many catheters, such as those for intermittent catheterization, are provided with a hydrophilic coating or the like, providing a smooth and slippery surface when wetted, for safe and comfortable insertion in the urinary canal.

Urinary catheters are conventionally provided as disposable, single-use items. A user will remove the catheter from a package of the assembly, use the catheter once, and then dispose of the catheter and the package. However, one time use of catheters makes catheterization relatively costly, and there is a risk that users may be tempted to use catheters more than once. This is particularly the case for users in countries and regions where there are no subvention programs. However, reusing a catheter which is not intended for such use involves risk, since the hydrophilic coating may have deteriorated from the first use, and since there is a risk that the catheter may be contaminated after the first use, thereby increasing the risk of urinary tract infections and the like.

On the other hand, reusable urinary catheters could be advantageous in reducing the costs for the users, and also for reducing the amount of waste created by the use of disposable catheters. Thus, from both an economical and environmental point of view, reusable catheter would be of advantage.

Some proposals of reusable urinary catheters have been made over the years. For example, U.S. Pat. No. 4,754,877, by the same applicant discloses a storage container for cleaning and storing of a reusable urinary catheter between use. Further, more recently filed WO 2020/252003, WO 2020/252032, WO 2020/252045 and WO 2020/263859 discloses different types of storage containers for sterilization or disinfection of used catheters.

However, there are still various problems that need to be solved to make reusable urinary catheters comfortable, reliable and safe to use, so that they become an accepted alternative for both users and prescribers. In particular, there is a need to solve the problems of how to ensure that the catheters when used can be properly disinfected, and also to prohibit too much deterioration of the hydrophilic coating of the catheter over time.

SUMMARY OF THE INVENTION

It is therefore an object of the disclosed embodiments to provide a reusable urinary catheter assembly which at least alleviates the above-discussed problems.

This object is obtained by means of a reusable urinary catheter assembly, and a corresponding method and hydration liquid, in accordance with the appended claims.

In accordance with a first aspect of the disclosed embodiments, there is provided a reusable urinary catheter assembly, comprising:
 a storage container defining a cavity;
 a hydration liquid within the cavity, the hydration liquid comprising a disinfection medium and at least one hydrophilic polymer, and wherein the viscosity of the hydration liquid is 40 cP or lower;
 a reusable urinary catheter including a shaft, wherein at least a part of the shaft is provided with a hydrophilic surface, the shaft being enclosed within the cavity in a storage position, wherein the hydration fluid hydrates and regenerates the hydrophilic surface and disinfects the catheter, the catheter being configured to be repeatedly inserted into and removed from the storage container.

According to another aspect of the disclosed embodiments, there is provided a hydration liquid for regeneration, disinfection and activation of a reusable hydrophilic urinary catheter, wherein the hydration liquid is an aqueous liquid comprising a disinfection medium and at least one hydrophilic polymer, wherein the concentration of hydrophilic polymer in the hydration liquid is at least 0.25 wt %, and wherein the viscosity of the hydration liquid is 40 cP or lower.

According to still another aspect of the disclosed embodiments, there is provided a method for preparing a reusable hydrophilic urinary catheter for repeated use, the method comprising:
 inserting a hydration liquid into a cavity of the storage container, the hydration liquid comprising a disinfection medium and at least one hydrophilic polymer, and wherein the viscosity of the hydration liquid is 40 cP or lower; and
 inserting the catheter into the storage container, before or after insertion of the hydration liquid, wherein the hydration liquid hydrates and regenerates a hydrophilic surface of the catheter and disinfects the catheter.

By disinfection medium is here meant a medium which eliminates many or all pathogenic microorganisms, but possibly with some exceptions, such as bacterial spores. The disinfection medium may also be referred to as a disinfectant. However, in some embodiments, the disinfection medium may destroy or eliminate all forms of microbial life, in which case the disinfection may also be referred to as sterilization, and the disinfection medium may be referred to as sterilization medium, a sterilant.

The viscosity is preferably measured at normal room temperature, and preferably at 25 deg. C.

It has been found by the present inventors that the addition of a certain amount of hydrophilic polymer(s) to the hydration liquid is of great advantage, since the hydrophilic surface of the catheter is hereby renewed and regenerated. It is believed that the hydrophilic polymer(s) in the hydration liquid becomes entangled and loosely bonded to the hydrophilic surface of the catheter when the catheter is stored in the hydration liquid. Hereby, a new outermost hydrophilic layer is built up after each use of the catheter, during storage in the hydration liquid. The catheter is hereby provided with a lower friction, in particular after having been used a number of times, and is consequently more comfortable to use repeatedly. The catheter, and in particular the hydrophilic surface, also becomes more durable, and can be used more times and during a longer period of time.

The reusable catheter can be reused many times in a safe, convenient and comfortable way. The catheter may consequently be reused for several days, weeks, months or even years.

In particular, it has been found that this effect is greater when the hydration liquid has a relatively high concentration of hydrophilic polymers, and the effect is further improved when the concentration of hydrophilic polymers increases. How high the concentration of hydrophilic polymer(s) is to some extent dependent on which hydrophilic polymer that is used, and in particular the molecular weight of the hydrophilic polymer(s). Hydrophilic polymers having a high molecular weight may be used in in lower concentrations, and still provide a very beneficial result, whereas hydrophilic polymers with a lower molecular weight should preferably be used at higher concentrations.

However, overall, the concentration of hydrophilic polymer in the hydration liquid should preferably be at least 0.25 wt %, and more preferably at least 0.5 wt %, and most preferably at least 1 wt %.

However, it has also been found that too high concentration of the hydrophilic polymers is detrimental. At higher concentrations of the hydrophilic polymers, the viscosity of the hydration liquid becomes too high, and this increases the friction of the hydrophilic surface of the catheter. Too high viscosity also makes the hydration liquid stick to the catheter, making it smudgy and difficult to handle and use. The hydration liquid, when having too high viscosity, may also remain in the drainage openings and/or the internal lumen of the catheter, thereby prohibiting flow of urine through the catheter.

Thus, the concentration of the hydrophilic polymers in the hydration liquid needs to be balanced so that the positive effects of the regeneration of the hydrophilic surface of the catheter is optimized, and on the other hand so that the drawbacks of a hydration liquid having too high viscosity is avoided. It has been found that the viscosity should be equal to or lower than 40 cP.

The hydration liquid is preferably an aqueous liquid. The aqueous liquid preferably contains at least 50 wt % of water, and preferably at least 60 wt %, and more preferably at least 70 wt %, and most preferably at least 80 wt %.

It has been found, and experimentally verified, that many different hydrophilic polymers may be used in the hydration liquid, and all providing a beneficial result. Preferably, the hydrophilic polymer comprises at least one of polyvinyl pyrrolidone (PVP), polyvinyl alcohol (PVA), polyethylene oxide (PEO) and hydroxypropyl methylcellulose (HPMC). However, other hydrophilic polymers may also be used. In embodiments, the hydrophilic polymer is preferably at least one of: polyvinyl compounds, polylactames, in particular such as polyvinyl pyrrolidones, polysaccharides, in particular heparin, dextran, xanthan gum, derivatised polysaccharides, hydroxy propyl cellulose, methyl cellulose, polyurethanes, polyacrylates, polyhydroxyacrylates, polymethacrylates, polyacrylamides, polyalkylene oxides, in particular polyethylene oxides, polyvinyl alcohols, polyamides, polyacrylic acid, copolymers of the previously mentioned polymers, copolymers of vinyl compounds and acrylates or anhydrides, copolymers of vinylpyrrolidone and hydroxy ethylmethyl acrylate, cationic copolymers of polyvinyl pyrrolidone and copolymer of polymethylvinyl ether and maleinic acid anyhydride. Most preferably, the hydrophilic polymer is polyvinylpyrrolidone.

In a particularly preferred embodiment, the hydrophilic polymer comprises PVP. In one embodiment, the PVP has a molecular weight in the range of 2-2000 kg/mol, and preferably in the range of 30-1800 kg/mol, and more preferably in the range of 40-1700 kg/mol. The PVP may e.g. be PVP K12, which has a molecular weight of 4-6 kg/mol, PVP K15, which has a molecular weight of 6-15 kg/mol, PVP K30, which has a molecular weight of 40-80 kg/mol, PVP K60, which has a molecular weight of 390-470 kg/mol, PVP K85, which has a molecular weight of 900-1200 kg/mol, and/or PVP K90, which has a molecular weight of 1000-1700 kg/mol. In a preferred embodiment, the hydration liquid comprises at least one of PVP K12, PVP K15, PVP K30 and PVP K90. In an even more preferred embodiment, the hydration liquid comprises at least one of PVP K30 and PVP K90.

In an embodiment, the hydration liquid comprises PVP with a molecular weight in the range of 40-80 kg/mol, and wherein the concentration of PVP in the hydration liquid is in the range of 5-20 wt %, and preferably 5-17 wt % and more preferably 10-16 wt %, and most preferably 12-15 wt %. Hereby, a very good regeneration of the hydrophilic surface is obtained, and at the same time, the viscosity falls within a good range for handling and use of the catheter.

In another embodiment, the hydration liquid comprises PVP with a molecular weight in the range of 1000-1700 kg/mol, and wherein the concentration of PVP in the hydration liquid is in the range 0.25-5.0 wt %, and preferably 1.0-5.0 wt %, and preferably 1.5-4.0 wt % and more preferably 2.0-3.0 wt %, and most preferably 2.2-2.8 wt %. Also here, a very good regeneration of the hydrophilic surface is obtained, and at the same time, the viscosity falls within a good range for handling and use of the catheter.

Generally, regardless of which hydrophilic polymer that is used, the concentration of hydrophilic polymer in the hydration liquid is preferably at least 1.0 wt %, and preferably at least 1.5 wt %, and preferably at least 2.0 wt % and more preferably at least 2.5 wt %. This is in particular the case for hydrophilic polymers having low or medium high molecular weight.

The viscosity of the hydration liquid is equal to or below 40 cP. At 40 cP the hydration liquid may still be used for wetting and regeneration of the hydrophilic surface, and would not prohibit use of the catheter for its intended purpose. However, some measures, such as scraping off excessive and remaining liquid, may be necessary. To this end, it is preferred to have a somewhat lower viscosity, such as 30 cP or lower, and preferably 25 cP or lower, and more preferably 20 cP or lower, and most preferably 15 cP or lower. At such lower viscosity ranges, handling and efficiency of the catheter for use become even better.

Since pure water at 20 deg. C. has a viscosity of about 1 cP, the inclusion of hydrophilic polymer in the hydration liquid makes the viscosity of this liquid become greater than 1 cP. Preferably, the viscosity of the hydration liquid is in the range of 2-40 cP, and preferably 5-30 cP, and more preferably 7-20 cP, and more preferably 10-15 cP, and most preferably 11-13 cP.

Different types of disinfection mediums may be used to kill bacteria remaining on the catheter after use, and to provide a disinfected, and possibly sterilized, catheter for the next use. In a preferred embodiment the disinfection medium comprises a chemical disinfectant.

In embodiments, the chemical disinfectant may comprise at least one of: benzalkonium chloride (BAC), sodium hypochlorite, silver nitrate, povidone-iodine (PVP-iodine) and triclosan. However, other chemical disinfectants may also be used. In a preferred embodiment, the disinfection medium comprises BAC.

However, other disinfectants may also be used as the disinfection medium, such as nanoparticles with bactericidal effects. Examples of these include, but are not limited to, silver, zinc oxide and copper oxide.

In addition to the disinfection medium, and to provide even more efficient disinfecting, additional disinfecting may also take place when the catheter is arranged in the storage container, such as by irradiation, e.g. with UV radiation or visible light, heating, subjecting it to electric current or other forms of energy, etc.

The hydration liquid may further comprise a surfactant. It has been found that use of a surfactant in the hydration liquid makes the regeneration process quicker and more efficient. A total concentration of surfactant(s) is preferably in the range of 0.01-0.5 wt %. The surfactant may be a non-ionic surfactant.

By "surfactant" is in the present application meant all molecules which have surface active properties, and which can decrease the surface tension or improve wetting by a liquid on a substrate.

The surfactant(s) are preferably organic compound(s), and are amphiphilic, which means that they contain both hydrophobic groups (their tails), usually a long alkyl chain, attached to hydrophilic or water solubility enhancing functional groups (their heads). Therefore, the surfactant(s) contains both a water-insoluble (or oil-soluble) component and a water-soluble component. Surfactants will diffuse in water and adsorb at interfaces between air and water or at the interface between oil and water, in the case where water is mixed with oil.

The surfactant is preferably water soluble.

Further, the surfactant is preferably non-ionic. Hereby, the interaction with human tissue is limited, and the surfactant will also not interact with e.g. ionic substances, pH buffers and similar optional additives. However, other surfactants may also be used, such as zwitterionic, anionic or cationic. Further, the surfactant preferably has relatively large chains/molecules, which further reduces any potential interaction with human tissue.

Examples of ionic surfactants that may be used in the wetting liquid and/or the hydrophilic coating/surface include one or more of alkyl sulphates (such as sodium dodecylsulphates), sodium cholate, bis(2-ethylhexyl)sulphosuccinate sodium salt, quaternary ammonium compounds, such as cetyltrimethylammonium bromide or chloride, lauryldimethylamine oxide, N-lauroylsarcosine sodium salt and sodium deoxycholate.

Examples of non-ionic surfactants that may be used in the wetting fluid and/or the hydrophilic coating/surface include one or more of alkylpolyglucosides, branched secondary alcohol ethoxylates, ethylene oxide/propylene oxide copolymers, nonylphenol ethoxylates, octylphenol ethoxylates, and specialty alkoxylates, such as Tween 80 and Tween 20.

Other examples of surfactants that may be used in the wetting fluid and/or the hydrophilic coating/surface include, but are not limited to, one or more of saponified coconut oil, vitamin E, polyoxyethylene sorbitan, monolaurate, sodium dodecyl sulfate, polysorbate, L-a-phosphatidylcholine, lecithin, stearyl stearate, sodium stearate, sodium laurate, sodium myristate, sodium myristate, sodium palmitate, sodium oleate, polyethylene glycol monododecyl ether, glycolic acid ethoxylate lauryl ether, glycolic acid ethoxylate oleyl ether, ethylene glycol monododecyl ether, polyoxyethylene glycerol ester, polyglyceryl esters, diglyceryl diisostearate, diglyceryl monolaurate, diglyceryl monooleate, docusate sodium, dioctyl sulfosuccinate sodium salt, dioctyl sodium sulfosuccinate, sodium dodecylbenzenesulfonate, perfluorobutane sulfonic acid, 3-sulfopropyl ethoxylate laurylphenly ether, lauric acid sodium salt, N-acylsarcosine sodium salt, and N-lauroylsarcosine sodium salt, and different types of cellulose derivatives, such as hydroxypropyl cellulose and hydroxypropyl methyl cellulose.

In preferred embodiments, the surfactant is one or more of Tween 80, Brij 35, all commercially available from Sigma Aldrich, TEGO Betain F50, commercially available from Evonik Industries, Kolliphor P188, Kolliphor P407, both commercially available from BASF, and HPMC 4M, commercially available from DuPont/Dow Chemicals.

The hydration liquid may further comprise a pH buffer, to ensure that the pH of the fluid is maintained in a preferred range, such as in the range of 4-8. The pH buffer may be citric acid, but other buffers may also be used, such as acetic acid, phosphate buffer, carboxylic acids, amino acids, aminosulphonic acids and inorganic acids.

The hydration liquid may further comprise other additives, such as an osmolality increasing agent, e.g. sodium chloride.

The hydrophilic surface of the catheter preferably comprises polyvinylpyrrolidone (PVP).

The hydrophilic surface may be arranged as a hydrophilic coating arranged on a substrate of the urinary catheter, as is per se well known in the art. However, the hydrophilic surface may alternatively be arranged as an integrated part of the urinary catheter, such as an integrated layer, or alternatively, the entire shaft of the urinary catheter may be made of a hydrophilic material. The hydrophilic coating/surface is preferably arranged to provide low friction when wetted.

The hydrophilic coating/surface may be a surface provided with a hydrophilic coating, for example made in accordance with EP 0 093 093 and EP 0 217 771, said documents hereby being incorporated by reference in their entirety.

Even though PVP is the preferred hydrophilic material of the hydrophilic surface, other hydrophilic materials may be used, such as hydrophilic polymers selected from polyvinyl compounds, polysaccharides, polyurethanes, polyacrylates or copolymers of vinyl compounds and acrylates or anhydrides, especially polyethyleneoxide, heparin, dextran, xanthan gum, polyvinyl alcohol, hydroxy propyl cellulose, hydroxy propyl methyl cellulose, methyl cellulose, copolymer of vinylpyrrolidone and hydroxy ethylmethyl acrylate or copolymer of polymethylvinyl ether and maleinic acid anyhydride. Further, hydrophilic coating/surface is to be understood in a broad sense, and in embodiments the hydrophilic coating/surface may comprise an entire insertable section of the urinary catheter formed of a hydrophilic material.

In preferred embodiments, the urinary catheter is a urinary catheter for intermittent, short time use. The term "short term use" indicates a use that is limited in time, and in particular limited to a time period of less than 15 minutes, and preferably less than 10 minutes, and most preferably less than 5 minutes.

In the present application, the term "proximal" is used to indicate the end or portion of the catheter that is inserted into the body of the user, i.e. the end or portion of the catheter that during use is closer in proximity to the user's body and/or initially enters the user's body upon insertion. The term "distal" is used to refer to an end or portion of the catheter that is opposite the proximal end or portion and is typically further away from the user's body. For the sake of consistency, when the terms "distal" and "proximal" are used in the context of other components which are not intended for introduction into the user's body, "proximal" refers to the end or portion that is closer to the proximal end of the catheter, while "distal" refers to an end or portion located opposite to such proximal end or portion.

The urinary catheter assembly comprises a storage container, such as a package or case, for accommodating the hydration liquid, and also, during storage, in particular between uses, at least the insertable part of the urinary catheter. In one embodiment, the storage container entirely encloses the urinary catheter. In such embodiments, the storage container may be provided with a re-openable closure, such as a cap. However, it is also possible to have the non-insertable part wholly or partly arranged outside the storage container. In such an embodiment, the exposed part of the urinary catheter, residing outside the storage container, may form a closure of the storage container.

The urinary catheter may be arranged immersed in the hydration liquid already from the start, i.e., prior to the first use. However, prior to the first use, the hydration liquid may also be kept separated from the catheter. For example, the hydration liquid may be arranged in a separate compartment or container of the assembly, and released into the storage container, where the catheter has been initially, after the first use. In another embodiment, the urinary catheter assembly comprises an additional container for housing the catheter before the first use, and a storage container containing the hydration liquid, and in which the catheter can be stored subsequent to the first use. The hydration liquid may also be provided in a separate container, such as in a bottle, so that the storage container can be sufficiently filled, and possibly refilled, during extended use.

The storage container is preferably impermeable to the wetting liquid, and preferably made of a liquid impermeable material. This ensures that liquid does not penetrate out from the storage container during storage, and enhances the shelf-life of the product. However, in embodiments where the hydration liquid is e.g. initially kept separated from the catheter, the material need not be totally liquid impermeable.

The urinary catheter assembly may be provided to a user in a disposable outer package. This disposable outer package may comprise the urinary catheter, the storage container and the hydration liquid in various configurations. For example, the urinary catheter and the hydration liquid may both be arranged in the storage container already in the outer package. However, the outer package may also enclose one or both of the urinary catheter and the hydration liquid separated from the storage container. For example, the urinary catheter may be arranged outside the storage container in the outer package, loosely or in a separate package. The outer package may also comprise more than one urinary catheter, whereby the first catheter can be discarded after a period of use, and be replaced by the next. For example, the outer package may comprise 2, 5, 10 or even more catheters.

Additionally, or alternatively, the hydration liquid may be provided in a separate container, such as a bottle, to be poured into the storage container after the first use, or immediately prior to the first use, for wetting of the catheter.

The reusable catheter may be used multiple times and may then be discarded for a new catheter, for use in the same storage container, or a new urinary catheter assembly.

The urinary catheter may have a connector, funnel shaped end or flared end arranged at the non-insertable, distal part, such as a flared connector. The catheter preferably has an internal lumen, extending from one or more drainage openings, so-called eyes or eyelets, arranged at or in the vicinity of the proximal insertion end, to a discharge outlet arranged at or in the vicinity of the distal end. A drainage opening may be arranged at the proximal tip of the elongate shaft, i.e. forming a centrally arranged opening in the longitudinal extension of the internal lumen. Additionally, or alternatively, one or more drainage openings may be formed in the sidewall of the elongate shaft, to debouch in a direction radially outwards. In one embodiment, the elongate shaft has a rounded, closed proximal end, and one or more drainage openings arranged in the sidewall of the elongate shaft.

A part of, or the whole, catheter shaft may form an insertable part or insertable length of the catheter. At least the insertable part may be provided with the hydrophilic coating/surface, or in other ways been provided with a hydrophilic coating/surface, which exhibits a lowered friction when wetted. Further, the distal part may, at least on a part thereof, have larger cross-sectional dimensions than the catheter shaft. The distal part may e.g. be flared or funnel shaped, increasing in dimension towards the distal end, thereby enabling connection of a tube, collection bag or the like.

These and other aspects of the disclosed embodiments will be apparent from and elucidated with reference to the embodiments described hereinafter.

BRIEF DESCRIPTION OF THE DRAWINGS

For exemplifying purposes, the disclosed technology will be described in closer detail in the following with reference to embodiments thereof illustrated in the attached drawing, wherein:

FIG. 1 is a cross-sectional view of a reusable urinary catheter assembly in accordance with an example embodiment.

DETAILED DESCRIPTION OF PREFERRED EMBODIMENTS

In the following detailed description preferred embodiments of the disclosed technology are exchangeable between the embodiments and may be combined in different ways, unless anything else is specifically indicated. It may also be noted that, for the sake of clarity, the dimensions of certain components illustrated in the drawings may differ from the corresponding dimensions in real-life implementations of the invention, e.g., the length of the medical device, etc. Still further, even if the detailed discussion in the following relates to a urinary catheter assembly, it is to be acknowledged that the same principles may be used for assemblies also for other hydrophilic catheters, as well as for assemblies for other hydrophilic medical devices.

A urinary catheter assembly 1 as illustrated in FIG. 1 comprises a catheter 2 having an insertable section 21, comprising an insertable, proximal part, with an insertion tip, on a catheter shaft, and a non-insertable section 22, a distal part, forming a connector part. The non-insertable section 22 preferably has a larger diameter than the insertable section 21 at least on a part thereof (see, e.g., section 24). The rear end 5 of the non-insertable section may be flared or funnel-shaped, and may be arranged to be connected to a tapered connection part of a urine collection bag or the like. However, the non-insertable section may alternatively have a relatively uniform cross-sectional area.

At least a part of the insertable section 21 forms an elongate shaft with an insertable length to be inserted into a natural or artificial body opening of a user, such as into a urethra of the user.

The insertable section comprises an insertion tip, which may be a closed, rounded end. Further the insertable section may comprise one or several drainage openings 23, arranged in the vicinity of the insertion tip, so called catheter eyes or eyelets, leading into a lumen extending through the catheter, and into a discharge outlet arranged at the rearward end of the non-insertable section 22.

The insertable section may be 80-140 mm for a female user and 200-350 mm for a male user.

The insertable section 21 may comprise a hydrophilic coating/surface, and form a hydrophilic catheter, as is per se well known in the art. The hydrophilic coating/surface may be in the form of a hydrophilic coating, for example PVP, and which provides a low-friction surface when wetted with a wetting fluid. Even though PVP is the preferred hydrophilic material, other hydrophilic materials may be used, as exemplified in the foregoing.

The catheter is intended for repeated use, and between the use periods, the catheter is intended to be stored in a storage container, so that at least the insertable part of the catheter is in contact with a hydration liquid. The hydration liquid serves to activate and regenerate the hydrophilic surface of the catheter, and also to disinfect the catheter for a subsequent new use.

In the storage position, the catheter is accommodated in a storage container 3, forming a closed cavity in which at least the insertable section of the catheter is arranged. In the illustrative examples, the entire catheter is arranged within the storage container. The cavity is preferably impermeable to the hydration liquid. The storage container is preferably, at least in most parts, made of a relatively rigid material. However, the storage container may also be made of a flexible material, such as foil. The storage container may be transparent, but may alternatively be opaque or semi-opaque. The storage container may be in the form of a tube or hose, a bottle, a case, or the like. The storage container is preferably arranged to surround the catheter relatively narrowly.

The storage container may e.g. be made of a material such as PVC plastics and high density polyethylene (HDPE). However, other materials are also feasible. For example, many other polymer materials and composite materials are feasible. The container may also comprise fibers, such as a fiber based material. Further, many other types of materials may also be used, in particular for embodiments where the storage container should be reused many times, and for many catheters. For such embodiments in particular, the storage container can be made of more durable, and possibly more rigid materials, which are easier to wash and clean, such as metal, glass, ceramics, and the like.

The storage container may be arranged to receive the catheter in a relatively straight configuration. However, alternatively, the storage container may be arranged to accommodate the catheter in a curved or bent configuration, to provide a more compact storage container.

The storage container may comprise an opening, preferably arranged above or overlying the non-insertable section 22 of the catheter. The opening may be provided with a closure 31, such as a cap or a lid. The closure may be connected to the opening by means of a thread, a friction fit, or the like. The closure can, thus, be removed to open the opening, for extraction of the catheter for use, and then again be closed when the catheter has been used, and then reinserted into the storage container.

The closure can, e.g., be made of a relatively rigid material, such as a polymeric material, and preferably closes off the opening so that when the catheter is stored in the storage container, hydration liquid does not leak from the opening.

During use, the storage container is at least partly filled with the above-discussed hydration liquid 4 arranged to encircle and immerse at least a part of the insertable part when the catheter is arranged in the storage container, and preferably at least the whole insertable part.

The catheter can be inserted into and removed from the storage container repeatedly, for repeated use of the catheter.

As discussed in the foregoing, the hydration liquid comprises water, to wet and activate the hydrophilic surface of the catheter, a hydrophilic polymer, arranged to regenerate the hydrophilic surface of the catheter between use periods, and a disinfection medium, to disinfect, and possibly sterilize, the catheter before the next use.

In embodiments, the hydration liquid may also comprise other additives, such as surfactant(s), osmolality increasing agent(s), pH buffer(s), etc.

EXPERIMENTAL RESULTS

In the following, some experimental tests will be discussed.

In a first line of experiments, the viscosity at 25 degrees Celsius of the hydration liquid was evaluated. Here, hydration liquids containing various concentrations of a hydrophilic polymer were used. The hydrophilic polymer used for these tests was PVP K30, having a molecular weight of 40-80 kg/mol. The hydrophilic polymer was mixed with water with a magnetic stirrer. The viscosity of the liquids was determined with a viscometer. The hydration liquid was then used as a storage liquid for the hydrophilic urinary catheters. The hydration liquid was arranged in a storage container together with a urinary catheter. The urinary catheters were then removed from the hydration liquid, and the friction and feel of the catheter surface were evaluated manually. It was found that conventional friction measurements could not be used, since the liquid remaining on the surface gave misleading results. Instead, the friction and feeling of the catheters were evaluated manually, by experienced testers. The manual feel of the catheter surfaces was evaluated immediately after removal from the storage container, and also after having scraped off excess liquid from the surface. The viscosity, concentration and manual evaluation of the different PVP solutions are shown in Table 1.

TABLE 1

The viscosity of the PVP K30 solutions with varying polymer concentration.

| Sample | PVP K30 concentration (%) | Viscosity (cP) | Manual evaluation before scraping | Manual evaluation after scraping |
|---|---|---|---|---|
| 1 | 5 | 2.6 | Good | Good |
| 2 | 10 | 5.6 | Good | Good |
| 3 | 15 | 11.9 | Good, but small amount of liquid remaining | Good |
| 4 | 18 | 17.8 | Good, but liquid remaining | Good |
| 5 | 21 | 28.1 | Acceptable, but much liquid remaining | Acceptable, but liquid still remaining |
| 6 | 25 | 47.2 | Acceptable, but much liquid remaining | Poor, and liquid remaining |
| 7 | 30 | 94.1 | Not acceptable, very much liquid remaining | Poor, and liquid remaining |
| 8 | 35 | 195 | Not acceptable, very much liquid remaining | Very poor, and liquid remaining |
| 9 | 40 | 534 | Not acceptable, very much liquid remaining | Very poor, and liquid remaining |
| 10 | 45 | 1067 | Not acceptable, very much liquid remaining | Very poor, and liquid remaining |

Thus, it has been found that the viscosity increases rapidly and exponentially when the concentration of the hydrophilic polymer increases. Roughly, the viscosity doubles for every 5% increment in PVP K30 concentration.

From the evaluations it may be concluded that a hydration liquid having a viscosity of at most 40 cP is acceptable, but even better results are achieved when the viscosity is 30 cP or lower, and preferably 25 cP or lower, and more preferably 20 cP or lower, and most preferably 15 cP or lower. It may also be concluded that the viscosity of the hydration liquid should preferably be in the range of 2-40 cP, and preferably 5-30 cP, and more preferably 7-20 cP, and more preferably 10-15 cP, and most preferably 11-13 cP.

In another line of tests, different hydrophilic polymers were tested to evaluate their suitability for use in a hydration liquid to regenerate a hydrophilic surface of a urinary catheter after use. The catheters were stored in the different hydration liquids between uses, and were a number of times a day removed and tested. The tests were made manually, simulating the abrasion occurring during an insertion into a real urethra, and the feel and slipperiness of the catheter were evaluated. As a benchmark, the manually evaluated feel of a commercially available LoFric® catheter was used. The catheters were each time graded from 9-1, where 9 was equal to the feel of the benchmark catheter. The grades 9-7 was considered very good, 6-4 to be acceptable, and grades 3-1 to be poor, and unfit for use as a urinary catheter. The results of these measurements are shown in Table 2 below.

TABLE 2

Manual evaluation of friction during repeated use.

| Additive | Concentration (%) | Average molecular weight of additive (kg/mol) | Number of use times of at least grade 9-7 | Number of use times of at least grade 6-4 |
|---|---|---|---|---|
| PEO | 4.38 | 100 | 19 | 22 |
| HPMC | 4.0 | 10 | 15 | 19 |
| PVA | 2.79 | 166 | 19 | 23 |
| PVP K12 | 34 | 2.5 | 16 | 19 |
| PVP K30 | 15 | 49 | 20 | 23 |
| PVP K90 | 2.52 | 1050 | 20 | 23 |
| Glycerol | 64.5 | 0.092 | 4 | 8 |
| No additive | N/A | N/A | 8 | 13 |

The concentrations of the additives were all chosen to provide a viscosity within the preferred range of 11.5-12 cP. It was found that hydrating liquids comprising hydrophilic polymers provided a prolonged durability of the catheters, thereby making them better suited for use with reusable catheter, compared to hydrating fluids comprising e.g. glycerol or without additives.

From this it may be concluded that all the examples having been immersed in a hydration liquid comprising a hydrophilic polymer between uses were significantly better for repeated use than when immersed in plain water or water with other additives, such as glycerol. It is believed that the hydrophilic polymer in the hydration liquid regenerates the hydrophilic surface of the catheter after each use, thereby making it better for subsequent use. The regeneration seems to be especially good when different types of PVP is used, but also for PVA and PEO.

In another line of experiments, hydration liquids with different concentrations of some of the hydrophilic polymers were evaluated. Again, the catheters were stored in the different hydration liquids between uses, and were a number of times a day removed and tested. The tests were made manually, simulating the abrasion occurring during an insertion into a real urethra, and the feel and slipperiness of the catheter were evaluated. As a benchmark, the manually evaluated feel of a commercially available LoFric® catheter was used. The catheters were each time graded from 9-1, where 9 was equal to the feel of the benchmark catheter. The grades 9-7 was considered very good, 6-4 to be acceptable, and grades 3-1 to be poor, and unfit for use as a urinary catheter. The results of these measurements are shown in Table 3 below.

TABLE 3

Manual evaluation of friction during repeated use.

| Additive | Concentration (%) | Average molecular weight of additive (kg/mol) | Number of use times of at least grade 9-7 | Number of use times of at least grade 6-4 |
|---|---|---|---|---|
| PVP K12 | 15 | 2.5 | 9 | 11 |
| PVP K12 | 34 | 2.5 | 16 | 19 |
| PVP K30 | 2 | 49 | 9 | 12 |
| PVP K30 | 5 | 49 | 10 | 14 |
| PVP K30 | 15 | 49 | 20 | >23 |
| PVP K90 | 0.25 | 1050 | 11 | 16 |
| PVP K90 | 0.5 | 1050 | 11 | 15 |
| PVP K90 | 1.0 | 1050 | 14 | 21 |
| PVP K90 | 2.52 | 1050 | 20 | 23 |
| PVP K12 + K30 | 5/10 | 2.5/49 | >23 | >23 |
| PVP K30 + surfactant | 15/0.01 | 49 | >23 | >23 |
| Glycerol | 64.5 | 0.092 | 4 | 8 |
| No additive | N/A | N/A | 8 | 13 |

From this it may be concluded that all the examples having been immersed in a hydration liquid comprising a hydrophilic polymer between uses were significantly better for repeated use than when immersed in plain water or water with other additives, such as glycerol. It was found that higher concentrations of hydrophilic polymer in the hydration liquid improved regeneration, and thus improved the possibilities of repeated use. It is therefore believed that a balance need to be found between as high as possible concentration of hydrophilic polymer to improve regeneration, and to keep the concentration of hydrophilic polymers sufficiently low to avoid too high viscosity.

It was further found that a mix of PVP having different molecular weights could be beneficial.

It was further found that an addition of a small amount of surfactant can be used, and would further improve the regeneration properties of the hydration liquid.

In another line of experiments, hydration liquids with different types of disinfection mediums were used, and evaluated in respect of the disinfection effect. The hydration liquid comprised 5 wt % of PVP K30, and various disinfection mediums. As comparative examples, a hydration liquid with PVP K30 but without any disinfection medium was used, as well as a hydration liquid only comprising water.

For the tests, catheters were first activated in a hydration liquid containing a disinfectant. Thereafter, the catheters were immersed in an *E. coli* suspension. The catheters were then rinsed in plain water, before again being immersed in the same hydration liquid used for the activation for 4 hours. Thereafter, the catheters were transferred into a growth medium and incubated at 37 deg. C. for 19.5 hours. After this, it was determined whether, or not, bacterial growth had occurred during incubation. The results of these measurements are shown in Table 4 below.

TABLE 4

Manual evaluation of friction during repeated use.

| Disinfection medium | Concentration of disinfection medium (wt %) | Result after incubation |
|---|---|---|
| Benzalkonium chloride | 0.025 | No growth |
| Benzalkonium chloride | 0.1 | No growth |
| Sodium hypochlorite | 0.02 | No growth |
| Silver nitrate | 0.05 | No growth |
| Silver nitrate | 0.2 | No growth |
| PVP-iodine | 1 | No growth |
| PVP-iodine | 5-7.5 | No growth |
| Triclosan | 0.075 | No growth |
| Triclosan | 0.3 | No growth |
| Control - water + PVP K30 | — | Growth |
| Control - only water | — | Growth |

These measurements showed that all the tested disinfection mediums were effective to reduce bacterial growth, and thereby to sterilize the catheters in a limited time. The control experiments show that in case no disinfection medium is used, a bacterial growth will occur.

CONCLUDING REMARKS

Specific embodiments of the invention have now been described. However, several alternatives are possible, as would be apparent for someone skilled in the art. For example, many other hydrophilic polymers than the ones mentioned above may be used, as well as other disinfecting mediums, etc. Further, other additives, such as surfactants, can be used, and in various concentrations. Such other additives may be beneficial in certain circumstances, but may not be necessary in other.

Such and other obvious modifications must be considered to be within the scope of the present invention, as it is defined by the appended claims. It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting to the claim. The word "comprising" does not exclude the presence of other elements or steps than those listed in the claim. The word "a" or "an" preceding an element does not exclude the presence of a plurality of such elements. Further, a single unit may perform the functions of several means recited in the claims.

What is claimed is:

1. A reusable urinary catheter assembly, comprising:
a storage container defining a cavity;
a hydration liquid within the cavity, the hydration liquid being an aqueous hydration liquid comprising: at least 50 wt % water, a disinfection medium and at least one hydrophilic polymer, wherein a viscosity of the hydration liquid is 40 cP or lower, wherein the at least one hydrophilic polymer comprises PVP and wherein a concentration of PVP in the hydration liquid is between 10-16 wt %;
a reusable urinary catheter including a shaft, wherein at least a part of the shaft is provided with a hydrophilic surface, the shaft being enclosed within the cavity in a storage position, wherein the hydration fluid hydrates and regenerates the hydrophilic surface and disinfects the reusable urinary catheter, the reusable urinary catheter being configured to be repeatedly inserted into and removed from the storage container.

2. The reusable urinary catheter assembly of claim 1, wherein the PVP has a molecular weight in the range 2-2000 kg/mol.

3. The reusable urinary catheter assembly of claim 1, wherein the PVP has a molecular weight in the range of 40-80 kg/mol.

4. The reusable urinary catheter assembly of claim 1, wherein the PVP has a molecular weight in the range of 1000-1700 kg/mol.

5. The reusable urinary catheter assembly of claim 1, wherein the PVP has a molecular weight in the range of 1000-1700 kg/mol.

6. The reusable urinary catheter assembly of claim 1, wherein the viscosity of the hydration liquid is 30 cP or lower.

7. The reusable urinary catheter assembly of claim 1, wherein the viscosity of the hydration liquid is 20 cP or lower.

8. The reusable urinary catheter assembly of claim 1, wherein the viscosity of the hydration liquid is in the range of 2-40 cP.

9. The reusable urinary catheter assembly of claim 1, wherein the viscosity of the hydration liquid is in the range of 7-20 cP.

10. The reusable urinary catheter assembly of claim 1, wherein the disinfection medium comprises a chemical disinfectant.

11. The reusable urinary catheter assembly of claim 10, wherein the chemical disinfectant comprises at least one of: benzalkonium chloride (BAC), sodium hypochlorite, silver nitrate, povidone-iodine (PVP-iodine) or triclosan.

12. The reusable urinary catheter assembly of claim 1, wherein the disinfection medium comprises benzalkonium chloride BAC.

13. The reusable urinary catheter assembly of claim 1, wherein the hydration liquid further comprises a surfactant.

14. The reusable urinary catheter assembly of claim 13, wherein a total concentration of the surfactant is in the range of 0.01-0.5 wt %.

15. The reusable urinary catheter assembly of claim 13, wherein the surfactant is a non-ionic surfactant.

16. A method for preparing a reusable hydrophilic urinary catheter for repeated use, the method comprising:
    inserting a hydration liquid into a cavity of a storage container, the hydration liquid being an aqueous hydration liquid comprising at least 50 wt % water, a disinfection medium and at least one hydrophilic polymer, wherein a concentration of the at least one hydrophilic polymer in the hydration liquid is between 10-16 wt % and wherein a viscosity of the hydration liquid is 40 cP or lower; and
    inserting the reusable hydrophilic urinary catheter into the storage container, before or after insertion of the hydration liquid, wherein the hydration liquid hydrates and regenerates a hydrophilic surface of the reusable hydrophilic urinary catheter and disinfects the reusable hydrophilic urinary catheter.

17. The reusable urinary catheter assembly of claim 1, wherein the hydration liquid further comprises a pH buffer.

18. The reusable urinary catheter assembly of claim 1, wherein the at least one hydrophilic polymer of the hydration liquid comprises a mix of PVP having different molecular weights.

19. A reusable urinary catheter assembly, comprising:
    a storage container defining a cavity;
    a hydration liquid within the cavity, the hydration liquid being an aqueous hydration liquid comprising: at least 50 wt % water, a disinfection medium and at least one hydrophilic polymer, wherein a concentration of the at least one hydrophilic polymer in the hydration liquid is at least 0.25 wt % and wherein a viscosity of the hydration liquid is 40 cP or lower;
    a reusable urinary catheter including a shaft, wherein at least a part of the shaft is provided with a hydrophilic surface, the shaft being enclosed within the cavity in a storage position, wherein the hydration fluid hydrates and regenerates the hydrophilic surface and disinfects the reusable urinary catheter, the reusable urinary catheter being configured to be repeatedly inserted into and removed from the storage container.

20. The reusable urinary catheter assembly of claim 19, wherein the at least one hydrophilic polymer comprises at least one of polyvinyl pyrrolidone (PVP), polyvinyl alcohol (PVA), polyethylene oxide (PEO) or hydroxypropyl methylcellulose (HPMC).

21. The reusable urinary catheter assembly of claim 19, wherein the at least one hydrophilic polymer comprises PVP.

22. The reusable urinary catheter assembly of claim 21, wherein the at least one hydrophilic polymer of the hydration liquid comprises a mix of PVP having different molecular weights.

23. The reusable urinary catheter assembly of claim 19, wherein the disinfection medium comprises benzalkonium chloride BAC.

24. The reusable urinary catheter assembly of claim 19, wherein the hydration liquid further comprises a surfactant.

25. The reusable urinary catheter assembly of claim 19, wherein the hydration liquid further comprises a pH buffer.

* * * * *